United States Patent
Messenger et al.

(10) Patent No.: US 6,210,971 B1
(45) Date of Patent: Apr. 3, 2001

(54) ASSAY FOR THE DETECTION OF CREATININE

(75) Inventors: Koleen K. Messenger; Michael J. Pugia, both of Granger, IN (US)

(73) Assignee: Bayer Corporation, Elkhart, IN (US)

( * ) Notice: Subject to any disclaimer, the term of this patent is extended or adjusted under 35 U.S.C. 154(b) by 0 days.

(21) Appl. No.: 09/236,485

(22) Filed: Jan. 25, 1999

(51) Int. Cl.$^7$ ..................................................... G01N 33/00
(52) U.S. Cl. ........................... 436/98; 436/164; 436/166; 436/169; 436/904; 436/103; 422/56; 435/4; 435/28
(58) Field of Search ............................... 436/80, 98, 164, 436/166, 169, 174, 904, 103, 104; 422/55, 56; 435/4, 28; 558/156, 162, 209

(56) References Cited

U.S. PATENT DOCUMENTS

| | | | |
|---|---|---|---|
| 5,173,431 | * 12/1992 | Pugia et al. | 436/86 |
| 5,374,561 | * 12/1994 | Pugia | 436/98 |
| 5,385,847 | * 1/1995 | Yip et al. | 436/534 |
| 5,399,498 | * 3/1995 | Pugia | 436/86 |
| 5,464,777 | * 11/1995 | Yip | 436/98 |
| 5,527,708 | * 6/1996 | Blass | 436/98 |
| 5,733,787 | * 3/1998 | Messenger et al. | 436/98 |
| 6,001,656 | * 12/1999 | Cast et al. | 436/98 |

* cited by examiner

Primary Examiner—Maureen M. Wallenhorst
(74) Attorney, Agent, or Firm—Jerome L. Jeffers

(57) ABSTRACT

Disclosed is an improved method for the detection of creatinine in a fluid test sample by contacting the test sample with cupric ions, a hydroperoxide, citrate and an oxidizable dye which gives a colored response in the presence of oxygen free radicals and a pseudoperoxide. The improvement involves stabilizing the reagent formulation by the addition thereto of an ionizable phosphate containing compound such as phytic acid.

10 Claims, No Drawings

ASSAY FOR THE DETECTION OF CREATININE

BACKGROUND OF THE INVENTION

Peroxidase is an enzyme that catalyzes the oxidation of various compounds such as phenols and amines by peroxides. In addition, particular compounds have been termed pseudoperoxidases because they behave in a manner similar to the peroxidase enzyme by liberating oxygen from hydroperoxides and transferring the oxygen to certain acceptor compounds. Accordingly, the pseudoperoxidases are enzyme like in that they catalyze, or otherwise participate in, reactions between peroxides and oxidizable compounds. The pseudoperoxidases, which include hemoglobin and its derivatives, are regarded as peroxidatively active substances. For example, in the assay of urine for glucose the enzyme glucose oxidase, in the presence of oxygen, first converts the glucose in the urine to gluconic acid and hydrogen peroxide after which the peroxide enzyme which is included in the assay system catalyzes the interaction between the hydrogen peroxide (hydroperoxide) and an oxidizable dye, such as O-tolidine or tetramethylbenzidine, to cause the dye which is colorless in its reduced state to become colored thus providing a detectable response. The degree and intensity of the colored response are directly proportional to the amount of hydrogen peroxide generated by the glucose conversion, provided there is sufficient peroxidase present to catalyze the oxidation of the dye.

Similarly, a peroxidatively active substance such as hemoglobin or a derivative thereof can catalyze the interaction between a hydroperoxide and an oxidizable dye. In such interactions, the peroxidatively active substance imitates the peroxidase and catalyzes the interaction between the hydroperoxide and the oxidizable dye. The resulting interaction provides a detectable response, such as color transition, wherein the intensity of the response is indicative of the concentration of the peroxidatively active substance.

Creatinine is the end metabolite when creatine becomes creatine phosphate and is used as an energy source for muscle contraction. The creatinine produced is filtered by the kidney glomeruli and then excreted into the urine without reabsorption. The determination of creatinine in body fluids is useful for diagnosing muscle diseases or various kidney diseases such as nephritis and renal insufficiency. The first practical test for the determination of creatinine, known as the Jaffe method, involves the formation of the red-yellowish brown colored creatinine picrate by the bonding of picric acid and creatinine in an alkaline solution. A more recent method for creatinine determination is reported by Benedict and Behre in *J. Biol. Chem.*, 113:515 (1936) which involves the reaction of 3,5-dinitrobenzoic acid with creatinine in an alkaline medium. Each of these reactions require a high pH, i.e. on the order of 12–13, in order to deprotonate the creatinine so that the system can operate properly. Strongly basic substances such as alkali and alkaline earth metal hydroxides are typically used to maintain a suitably high pH in these reagent systems. Operating at such high pH values presents various difficulties, especially when an absorbant carrier such as filter paper or a porous film is used as carrier for the reagent system. This is the case because upon introduction of the alkali, the carrier tends to become brittle and it is difficult to obtain even distribution of the alkali throughout the carrier matrix. Furthermore, when the reagents are applied to the carrier in the form of a solution followed by evaporating the solvent to leave a dry residue, the dried alkali does not readily solubilize when contacted with a fluid such as a urine sample which is being examined for creatinine concentration.

In U.S. Pat. No. 5,374,561 there is described a method for the detection of creatinine in an aqueous medium which involves contacting the medium suspected of containing creatinine with cupric ions in the presence of a hydroperoxide and a redox indicator which provides a colored response in the presence of oxygen free radicals. Also included in the creatinine reagent formulation disclosed in this patent is citrate to prevent urine components other than creatinine from complexing with the cupric ions. This patent also presents a series of equations which are believed to represent the reaction which results in a detectable response for the determination of creatinine:

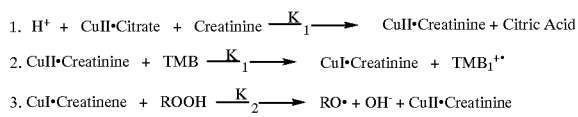

1. $H^+ + CuII\cdot Citrate + Creatinine \xrightarrow{K_1} CuII\cdot Creatinine + Citric Acid$
2. $CuII\cdot Creatinine + TMB \xrightarrow{K_1} CuI\cdot Creatinine + TMB_1^{+\cdot}$
3. $CuI\cdot Creatinene + ROOH \xrightarrow{K_2} RO\cdot + OH^- + CuII\cdot Creatinine$ In the foregoing scheme, reaction 1 represents the formation of the CuII. Creatinine complex from its resting state. Reaction 2 represents the oxidation of the TMB dye by the transfer of 1 electron from the TMB to the CuII. Creatinine complex to produce the non-reactive CuI form. Reaction 3 is the regeneration step whereby the CuI complex loses an electron to the peroxide to regenerate the CuII. An improved buffer system for this assay is disclosed in U.S. Pat. No. 5,733,787.

In order to increase the sensitivity of urinary assays and minimize the problem of high urine flow rates which result in urine dilution, analyte/creatinine ratios are used in urine analyte (e.g. protein) assays to normalize the urine concentration. Many clinically significant analytes are present in urine and urinalysis for them can be rendered more accurate by use of the creatinine ratio method. Among these analytes (sometimes referred to as the target analyte) are deoxypyridinoline, human serum albumin, drugs of abuse such as amphetamines, barbiturates and cocaine, clinically important protein markers such as prostate specific antigen; kidney disease proteins such as alpha-1-microglobulin, lactate dehydrogenase and N-acetyl-B-D-glucosamindase; pregnancy or fertility associated hormones such as human chorionic gonadotropin, follicle stimulating hormone and lutenizing hormone, markers of urinary tract infection such as Tamm-Horsfall protein or lipopolysaccharide, beta-2-microglobulin, amylase and chlamydial LPS.

In U.S. Pat. No. 5,173,431 there is disclosed a procedure for detecting proteins in fluids such as body fluids which involves contacting the fluid with a composition containing copper in a form capable of forming a copper/protein complex, which serves as a pseudoperoxidase, a peroxide and a redox indicator, which provides a detectable response when oxidized, together with an ionizable phosphate compound which can be phytic acid. This method does not require the presence of a citric acid since citric acid limits the formation of the copper/protein complex.

SUMMARY OF THE INVENTION

The present invention is an improvement in the method for the detection of creatinine in a fluid test sample which method involves contacting the test sample with cupric ions, a hydroperoxide, citrate and an oxidizable dye which provides a colored response in the presence of creatinine. The improvement comprises including in the assay formulation a stabilizing amount of an ionizable phosphate containing compound of formula I:

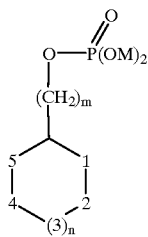
(I)

wherein 2, 3, 4 and 5 are selected from the group consisting of

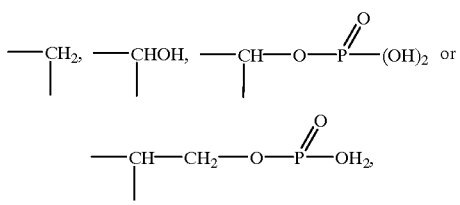

M is H or a group I or II metal, 1 is any of the above or —O— and m and n are independently 0 or 1.

DETAILED DESCRIPTION OF THE INVENTION

Referring to formula I, M is preferably hydrogen. However, salts in which M is a group I metal ion such as $Li^+$, $Na^+$, $K^+$ or a group II metal ion such as $Ca^+$ or $Mg^{++}$ may be used in this invention.

The creatinine assay to which the present invention is an improvement requires an assay medium containing cupric ions, a hydroperoxide, citric acid and an oxidizable dye which provides a colored response in the presence of creatinine.

The source of the cupric ion can be any soluble copper salt whose anion does not detrimentally interact with the reaction for the calorimetric determination of creatinine in the assay system. Suitable salts include copper sulfate, nitrate, oxide, hydroxide, phosphate, iodide, chloride, bromide, acetate or oxalate. Other soluble cupric salts may be used provided that they allow formation of the CuII.creatinine complex. Those salts whose anion binds too strongly to the copper will not allow the copper II.creatinine complex to form, and, accordingly, CuII complexes such as those formed between cupric ions and EDTA, HEDTA, EGTA and DTPA would not release sufficient CuII for the formation of the CuII.creatinine complex. It has been observed that the citrate and sulfate salts have the lowest blank reactivity, and they are preferred. Cupric citrate is particularly preferred since it exhibits the least blank reactivity to other urine components and the greatest formation of the CuII.creatinine complex as well as preventing copper/protein complex formation. Salts such as cupric 2,2'-bipyridine, which can oxidize the dye in the absence of creatinine, are less desirable due to their tendency to cause the assay to report false positives. When copper citrate is used as the cupric ion source, the concentration of citrate ion should be at least that of copper, and an excess of citrate ion is preferred to ensure complete complexation of CuII by the citrate and to prevent complexation of other species in the urine sample.

Typically, when urine is the aqueous fluid being tested, the concentration of cupric ion will be from 5 to 80 mM since the reference range of creatinine in urine is 3 to 20 mM. This range would vary in other fluids such as serum where one would preferably employ a concentration of cupric ion in the range of from 0.05 to 0.30 mM. The Cuprous ion tends to cause some background interference due to oxidation of the dye in the absence of creatinine. Accordingly, CuI salts cannot be used.

Suitable oxidizable indicators include, for example, benzidine; o-tolidine; a 3,3', 5,5'-tetraalkyl-benzidine wherein the alkyl group includes from one to about six carbon atoms, o-dianisidine; 2,7-di-aminofluorne; bis-(N-ethylquinol-2-one)-azine; (N-methylbenzthiazol-2-one)-(1-ethyl-3-phenyl-5-methyl-triazol-2-one)-azine or combinations thereof.

Suitable hydroperoxides for use in the present invention include cumene hydroperoxide; 5-butyl hydroperoxide; diisopropylbenzene hydroperoxide; 1-hydroxycyclohexane-1-hydroperoxide; 2,5-dimethyl-hexane-2,5-dihydroperoxide; paramenthane hydroperoxide; 1,4-diisopropylbenzene monohydroperoxide; p-t-butyl-isopropylbenzene hydroperoxide; 2-(α-hydroperoxyisopropyl)-6-isopropylnaphthalene; tetralin hydroperoxide or combinations thereof.

Typically, the reagent system, comprising the soluble copper salt, hydroperoxide and oxidizable indicator will be dissolved in water. However, organic solvents can be incorporated into the system provided they do not interfere with the assay mechanism. The concentration of the hydroperoxide and oxidizable indicator will normally range from 10 to 150 mM with a range of from 30 to 90 mM being preferred. The concentration of the hydroperoxide will normally range from 18 to 270 nM with a range of from 50 to 160 nM being preferred.

In the practice of the invention, the assay can be performed in either the wet or the dry (test strip) format. In carrying out the assay, the test sample is mixed with the copper salt, e.g. cupric citrate, the dye and the hydroperoxide at a buffered pH, preferably from 4.0 to 9.0, through the use of a reagent strip or aqueous and acetonitrile solutions of reagents. Reagent strips are prepared in the conventional manner of dipping an absorbant carrier into an aqueous solution of the cupric salt and buffers, drying the carrier and then dipping it into an organic solution of the dye and hydroperoxide with subsequent drying.

The use of phytic acid, and/or certain derivatives thereof as circumscribed by the foregoing formula I, has been found to have a stabilizing effect on the formulation for determining creatinine as previously described. This stabilization is manifested by the dye not being oxidized to form a color thereby leading to false positives. Without phytic acid or a derivative thereof corresponding to the foregoing formula, oxidation occurs in the absence of creatinine when the formulation is exposed to heat or moisture.

While there is no intent to be bound by any particular theory or mechanism of how the present invention accomplishes the desired result of improving the stability of the creatinine assay formulation, it is believed that cupric ion is converted to cuprous ion through exposure to oxygen, moisture and/or heat. The cuprous ion is highly reactive towards the oxidizable dye and hydroperoxide, e.g. TMB and DBDH even in the absence of creatinine. It is believed that the addition of phytic acid or derivative thereof stabilizes the cupric ion valence state through complexation and presents a greater barrier towards conversion by oxygen, moisture and heat. Furthermore, phytic acid and its derivatives do not prevent complexation of cupric ion by creatinine and allow the assay to function as a creatine detection method. Stronger complexation agents, such as EDTA, also stabilize the cupric ion valence state through complexation, but also prevent the complexation of cupric ion by creatinine. Simple phosphates such as glycerol-2-phosphate and sodium phosphate do not stabilize the cupric ion valence state.

The present invention can be performed as a solution assay by first mixing the copper salt, phytic acid, citrate and buffer with a specimen containing creatine and then adding the dye, e.g. TMB, and hydroperoxide, e.g. DBDH, in a polar solvent followed by measuring the spectral response at 660 nm. Typically, the reagent system is used as a test strip in the form of an absorbant bibulous or non-bibulous support to which the reagents are applied by dipping the strip in the reagent solution with subsequent evaporation of the carrier liquid. Typically, an aqueous solution is used although polar organic solvents such as methanol, ethanol and acetonitrile may be used as solvent for the reagents. The absorbant substrate used for the test strip is composed of materials commonly used as carriers such as paper, cellulose, fabrics made of synthetic resin, e.g. nylon or unwoven fabric. The absorbant material is typically bound to a layer of support material such as glass fiber or a synthetic polymer sheet to provide structural support.

The present invention is further illustrated by the following examples:

EXAMPLE I

The formulation for detecting creatinine according to the present invention was prepared by a two dip method in which a strip of Whatman 3 MM filter paper was dipped into a first solution followed by drying at 90° C. until dry ($\approx$5–10 minutes) and dipping into a second solution with subsequent drying.

The dipping solutions were formulated as follows:

| First Dip | | |
|---|---|---|
| Component | Concentration | Range of Concentrations |
| CuSO$_4$ | 30 mM | 0 to 80 mM |
| Citrate | 50 mM | 3 to 280 mM |
| Glycerol-2-phosphate | 500 mM | 250 to 1000 mM |
| SDS[1] | 0.14% (w/v) | 0 to 1.2% (w/v) |
| Phytic Acid | 50 mM | 5 to 500 mM* |
| pH | 6.84 | 4.0 to 9.0 |
| Water | q. s. | |

*25 to 125 preferred

| Second Dip | | |
|---|---|---|
| Component | Concentration | Concentrations |
| TMB[2] | 33 mM | 10 to 150 mM |
| DBDH[3] | 73 mM | 18 to 270 mM |
| Plasdone (PVP) | 0.5% (w/v) | 0 to 4.0% (w/v) |
| Triisopropanolamine Borate (TIB) | 63 mM | 0 to 250 mM |

| Second Dip -continued | | |
|---|---|---|
| Component | Concentration | Concentrations |
| Ethyl Orange Dye | 0.32% (w/v) | 0 to 2.0% (w/v) |
| Ethanol | q.s. | |

Strips prepared as described above were tested for open bottle use-life the determination of which involves leaving a bottle of strips open at 80% humidity for 24–48 hours and evaluating the effects on strip performance. The creatinine strip, without any phytic acid, showed changes in the dry pad color and strip performance; the strip turned brown due to over-oxidation after 24 hours. In order to evaluate the effects of different elements of the formulation on the dry color pad changes, strips were made which lacked certain components. These strips were stored uncapped at relatively high humidity and evaluated after 48 hours. The changes are summarized in Table 1.

TABLE 1

Visual Results of Open Bottle Use-Life Test

| Formulation | Description | Dry Pad Color Unexposed | Exposed |
|---|---|---|---|
| 25895-12-08 | no dye, Control | Pale Blue | Dirty Yellow |
| 25895-12-09 | no dye, no G-2-P | Pale Blue | Dirty Yellow |
| 25895-12-10 | no dye, no Cu-Cit | White | White |
| 25895-12-11 | no dye, no Cu-Cit, no DBDH | White | White |
| 25895-12-12 | no dye, no DBDH | Pale Blue | Pale Blue |
| 25895-12-13 | no dye, 55 mM DBDH | Pale Blue | Dirty Yellow (less than control) |
| 25895-12-14 | no dye, no TMB | Pale Blue | Pale Blue |
| 25895-28-16 | no dye, no phytic acid | Pale Green | Brown |
| 25895-28-17 | no dye, no HexSA | Pale Green | Medium Green |
| 25895-28-18 | no dye, no TIB | Pale Yellow | Light Green |

The results set out in Table 1 demonstrate that strips without phytic acid turn brown due to oxidation of TMB by copper sulfate and DBDH. When TMB, DBDH or copper sulfate are removed from the formulation no browning was observed. Brown strips are almost completely unresponsive to creatinine since TMB is consumed and is not able to react in the assay.

Furthermore, during development of the creatinine reagent, there was noted a large stability shift in the data collected during the accelerated heat stress. This shift would cause a 30 mg/dL reading to increase beyond an acceptable level and would be manifested as a loss of stability over the shelf life of the product. Table 2 presents data on the creatinine reagents stability with and without the addition of phytic acid.

TABLE 2

Improvement in Stability of the Creatinine Strip with the Addition of Phytic Acid

| storage temperature | time (days) | no phytic acid instrument value | sd | % shift | 50 mM phytic acid instrument value | sd | % shift |
|---|---|---|---|---|---|---|---|
| 25° C. | 1 | 438 | 15 | | 442 | 8 | |
| 25° C. | 7 | 403 | 13 | 8.6 | 445 | 6 | 0 |

TABLE 2-continued

Improvement in Stability of the Creatinine Strip with the Addition of Phytic Acid

| storage temperature | time (days) | no phytic acid instrument value | sd | % shift | 50 mM phytic acid instrument value | sd | % shift |
|---|---|---|---|---|---|---|---|
| 25° C. | 14 | 394 | 16 | 10.0 | 448 | 5 | 0 |
| 60° C. | 7 | 282 | 6 | 35.6 | 437 | 7 | 10.8 |

The addition of phytic acid decreased this stability shift over 2 weeks at 25° C. and after 1 week at 60° C. The instrument value is expressed in decode which is a number representing the reflectance of color from the reagent as measured by a CLINITEK® reflectance spectrometer. Lower numbers indicate that more color is generated. As the decode number decreases, the reflectance at 660 nm decreases due to color formation from the oxidation of TMB causing it to become blue at 660 nm and then brown at 450 nm.

What is claimed is:

1. In the method for the determination of creatinine in a fluid test sample which involves contacting the fluid test sample with a reagent composition comprising cupric ions, a hydroperoxide, citrate and an oxidizable dye which provides a colored response in the presence of oxygen free radicals and a pseudoperoxide and determining the concentration of creatinine in the fluid test sample by determining the intensity of the colored response and comparing this intensity to that obtained using fluid test samples containing known concentrations of creatinine; the improvement which comprises introducing a stabilizing amount of an ionizable phosphate containing compound having the formula:

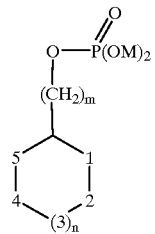

wherein 2, 3, 4 and 5 are selected from the group consisting of

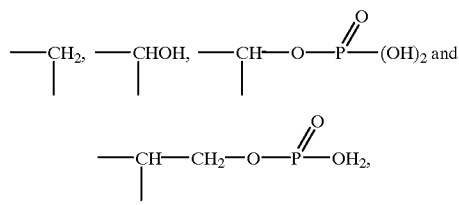

1 is any of the above or —O—, M is H or a group I or II metal, and m and n are independently 0 or 1, to the reagent composition to stabilize the reagent composition before contacting it with the fluid test sample by preventing the oxidation of the dye in the absence of the fluid test sample.

2. The method of claim 1 wherein the ionizable phosphate containing compound is phytic acid.

3. The method of claim 1 wherein M is hydrogen.

4. The method of claim 1 wherein the source of the cupric ion is cupric sulfate.

5. The method of claim 1 wherein the fluid test sample is urine and the concentration of cupric ions is 5 to 30 mM.

6. The method of claim 1 wherein the oxidizable dye is benzidine; o-tolidine; a 3,3', 5,5'-tetraalkylbenzidine wherein the alkyl group includes from one to about six carbon atoms, o-dianisidine; 2,7-diamino-fluorne; bis-(N-ethylquinol-2-one)-azine; (N-methyl-benzthiazol-2-one)-(1-ethyl-3-phenyl-5-methyl-triazol-2-one)-azine or a combination thereof.

7. The method of claim 1 wherein the hydroperoxide is cumene hydroperoxide; 5-butyl hydroperoxide; diisopropylbenzene hydroperoxide; 1-hydroxycyclohexane-1-hydroperoxide; 2,5-dimethyl-hexane-2,5-dihydroperox-ide; paramenthane hydroperoxide; 1,4-diisopropyl-benzene monohydroperoxide; p-t-butyl-isopropylbenzene hydroperoxide; 2-(α-hydroperoxyisopropyl)-6-isopropyl-naphthalene; tetralin hydroperoxide or a combination thereof.

8. The method of claim 1 wherein the reagent composition is incorporated into an absorbant carrier to form a test strip.

9. The method of claims 8 wherein the concentration of creatinine is combined with the concentration of a target analyte to obtain a ratio.

10. In a reagent composition for the determination of creatinine in a fluid test sample which composition comprises cupric ions, a hydroperoxide, citrate and an oxidizable dye which provides a colored response in the presence of oxygen free radicals and a pseudoperoxide; the improvement which comprises including a stabilizing amount of an ionizable phosphate containing compound having the formula:

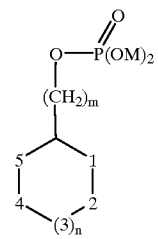

in the reagent composition before it is contacted with the fluid test sample so as to prevent the oxidation of the dye in the absence of the fluid test sample, wherein 2, 3, 4 and 5 are selected from the group consisting of

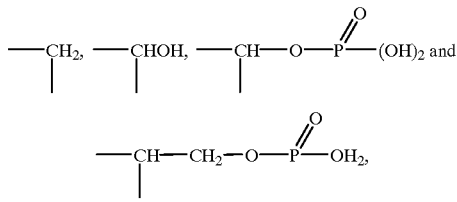

1 is any of the above or —O—, M is H or a group I or II metal, and m and n are independently 0 or 1.

* * * * *